(12) United States Patent
Bozzano et al.

(10) Patent No.: US 8,735,639 B2
(45) Date of Patent: May 27, 2014

(54) PREPARING A LIGHT-OLEFIN CONTAINING PRODUCT STREAM FROM AN OXYGENATE-CONTAINING FEED STEAM USING REACTORS DIRECTING A FLOW OF A FLUIDIZED DUAL-FUNCTION CATALYST SYSTEM

(75) Inventors: Andrea G. Bozzano, Northbrook, IL (US); Bryan K. Glover, Algonquin, IL (US); Peter R. Pujado, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 1063 days.

(21) Appl. No.: 12/755,632

(22) Filed: Apr. 7, 2010

(65) Prior Publication Data

US 2010/0204530 A1 Aug. 12, 2010

Related U.S. Application Data

(62) Division of application No. 11/461,288, filed on Jul. 31, 2006, now Pat. No. 7,722,825.

(51) Int. Cl.
*B01J 8/00* (2006.01)
*C07C 2/00* (2006.01)

(52) U.S. Cl.
USPC ........... 585/324; 585/327; 585/639; 585/640; 422/140; 422/142

(58) Field of Classification Search
USPC .......... 585/324, 327, 639, 640; 422/140, 141, 422/142
See application file for complete search history.

(56) References Cited

U.S. PATENT DOCUMENTS

| | | | |
|---|---|---|---|
| 6,497,812 B1 * | 12/2002 | Schinski | 208/131 |
| 7,230,151 B2 * | 6/2007 | Martens et al. | 585/324 |
| 7,317,133 B2 * | 1/2008 | Vora et al. | 585/327 |
| 7,405,337 B2 * | 7/2008 | Kalnes et al. | 585/640 |
| 7,582,268 B1 * | 9/2009 | Bozzano et al. | 422/610 |
| 7,722,825 B1 * | 5/2010 | Bozzano et al. | 422/141 |
| 2003/0234209 A1 * | 12/2003 | Smith et al. | 208/113 |
| 2005/0150817 A1 * | 7/2005 | Tallman et al. | 208/78 |
| 2006/0161035 A1 * | 7/2006 | Kalnes et al. | 585/639 |

* cited by examiner

*Primary Examiner* — Nina Bhat
(74) *Attorney, Agent, or Firm* — Arthur E Gooding

(57) ABSTRACT

The present process provides a method for converting an oxygenate-containing feed stream to an olefin-containing product stream. The method includes: (1) providing a first fluidized catalytic reactor for converting methanol to propylene, the first reactor having a fluidized catalyst system comprising a first catalyst and a second catalyst; (2) providing a second fluidized catalytic reactor communicating with the first fluidized catalytic reactor for cracking heavy olefins having four carbon atoms or greater into propylene, the second reactor having the fluidized catalyst system; (3) providing an oxygenate containing feed to the first reactor; and (4) fluidizing the catalyst system with the oxygenate containing feed.

5 Claims, 1 Drawing Sheet

PREPARING A LIGHT-OLEFIN CONTAINING PRODUCT STREAM FROM AN OXYGENATE-CONTAINING FEED STEAM USING REACTORS DIRECTING A FLOW OF A FLUIDIZED DUAL-FUNCTION CATALYST SYSTEM

This application is a Division of application Ser. No. 11/461,288 filed Jul. 31, 2006, now U.S. Pat. No. 7,722,825, the contents of which are hereby incorporated by reference.

FIELD OF THE INVENTION

The present invention relates generally to the use of two independent reactors for preparing a light-olefin containing product stream from an oxygenate containing feed stream. One reactor converts an oxygenate containing feed stream into a light-olefin containing product stream. A second reactor interconverts a heavy-olefin containing feed stream into a light-olefin product stream. Both reactors utilize a shared fluidized flow of a dual-function catalyst system. The catalyst system contains a zeolite molecular sieve catalyst and a non-zeolite molecular sieve catalyst.

BACKGROUND OF THE INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials. Thus, R & D personnel seek to use alternative feedstocks effectively and selectively to produce light olefins, thereby lessening dependence of the petrochemical industry on petroleum feedstocks. Much attention has been focused on the possibility of using hydrocarbon oxygenates and more specifically methanol or dimethylether (DME) as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established and typically involves the use of one or more of the following procedures: (1) manufacture of synthesis gas by any of the known techniques typically using a nickel or cobalt catalyst in a steam reforming step followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products in order to make an oxygenate to olefin (OTO) process. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. Two principal techniques are known in the art for conversion of methanol to light olefins (MTO). U.S. Pat. No. 4,387,263 discloses one MTO processes that utilizes a catalytic conversion zone containing a zeolitic type of catalyst system. The '263 patent reports on a series of experiments with methanol conversion techniques using a ZSM-5 type of catalyst system.

U.S. Pat. No. 4,587,373 discloses using a zeolitic catalyst system like ZSM-5 for purposes of making light olefins. The '373 Patent discloses diverting a portion of a methanol feed stream to a DME absorption zone to allow for downsizing of a scrubbing zone.

U.S. Pat. No. 5,095,163; U.S. Pat. No. 5,126,308 and U.S. Pat. No. 5,191,141 disclose an MTO conversion technology utilizing a non-zeolitic molecular sieve catalytic material. More particularly these patents disclose using a metal aluminophosphate (ELAPO) and more specifically a silicoaluminophosphate molecular sieve (SAPO) and even more specifically SAPO-34. This SAPO-34 material was found to have a very high selectivity for light olefins with a methanol feedstock and consequently very low selectivity for the undesired corresponding light paraffins and the heavier materials.

The classical OTO technology produces a mixture of light olefins primarily ethylene and propylene along with various higher boiling olefins. Although the classical OTO process technology possesses the capability of shifting the major olefin product recovered therefrom from ethylene to propylene by various adjustments of conditions maintained in the reaction zone, the art has long sought an oxygenate to propylene (OTP) technology that would provide better yields of propylene relative to the classical OTO technology. The driving force for this shift in emphasis towards propylene is the growth rate of the propylene market versus the growth rate of the ethylene market. The existing sources of propylene production in the marketplace are primarily based on conventional steam cracking of naphtha, LPG streams, propane streams and the like. Another principal source of propylene is produced in a fluid catalytic cracking (FCC) hydrocarbon conversion process in the modern day refinery.

US 2003/0139635A1 discloses a fixed bed methanol to propylene (MTP) process for selectively producing propylene from a feedstock of methanol and/or DME. This patent application discloses a flowscheme having an oxygenate to propylene (OTP) synthesis portion having three reactors in a parallel flow arrangement with respect to the oxygenate feed and utilize a steam diluent and fixed beds of oxygenate conversion catalysts. The reactors are connected in a serial flow arrangement with respect to the effluents of the first reactor and the second reactor. This patent application further discloses using a dual function OTP catalyst system including a pentasil-type catalyst (e.g., ZSM-5 or ZSM-11 type) having an alkali content less than 380 ppm and a zinc oxide content of less than 0.1 wt-% coupled with a restriction on cadmium oxide content of the same amount.

EP-B-1025068 discloses using two reaction zones to convert an oxygenate feed and a by-product fraction containing $C_4^+$ hydrocarbons to ethylene and propylene. This patent discloses that the two reaction zones allow for independent selection of catalyst and conversion conditions for each zone.

This '068 patent discloses using a non-zeolitic molecular sieve catalyst such as the preferred SAPO-34 for an oxygenate to light olefin reaction zone and either a non-zeolitic molecular sieve catalyst or a zeolitic catalyst such as the preferred ZSM-5 material for the auxiliary reaction zone which operates to convert the $C_4^+$ by-product fraction to the desired light olefin (i.e., $C_2$ and $C_3$ olefins). The '068 patent discloses using a circulating fluid bed or a riser reaction for the first reaction zone and a fluid bed or a fixed bed or a fixed tube reactor for the second reaction zone.

SUMMARY OF THE INVENTION

The present invention provides a reactor system for converting an oxygenate-containing feed stream to an olefin-containing product stream. The system includes: (1) a first fluidized catalytic reactor for converting methanol to propylene, the first reactor having a fluidized catalyst system comprising a first catalyst and a second catalyst; (2) a second fluidized catalytic reactor in at least partial fluid communication with the first fluidized catalytic reactor for cracking heavy olefins having four carbon atoms or greater into propylene, the second reactor having the fluidized catalyst system; (3) wherein the first catalyst is a non-zeolite molecular sieve catalyst; and (4) wherein the second catalyst is a zeolite molecular sieve catalyst.

The present invention further provides a reactor system for converting an oxygenate-containing feed stream to an olefin-containing product stream. The system includes: (1) a first fluidized catalytic reactor for converting methanol to propylene, the first reactor having a fluidized catalyst system comprising a first catalyst and a second catalyst; (2) a second fluidized catalytic reactor in at least partial fluid communication with the first fluidized catalytic reactor for cracking heavy olefins having four carbon atoms or greater into propylene, the second reactor having the fluidized catalyst system, the second fluidized catalytic reactor operated at a higher inlet temperatures than the first fluidized catalytic reactor; (3) a catalyst system regenerator in fluid communication with the first fluidized catalytic reactor and the second fluidized catalytic reactor; (4) wherein the first catalyst is a non-zeolite molecular sieve catalyst; and (5) wherein the second catalyst is a zeolite molecular sieve catalyst.

The present invention further provides a method for converting an oxygenate-containing feed stream to an olefin-containing product stream. The process includes: (1) providing a first fluidized catalytic reactor for converting methanol to propylene; (2) providing a second fluidized catalytic reactor in at least partial fluid communication with the first fluidized catalytic reactor for cracking heavy olefins having four carbon atoms or greater into propylene; (3) providing a catalyst system in a fluidized stream into the first fluidized catalytic reactor and into the second fluidized catalytic reactor, wherein the catalyst system comprises a first catalyst and a second catalyst, the first catalyst being a non-zeolite molecular sieve catalyst and the second catalyst being a zeolite molecular sieve catalyst; (4) providing the oxygenate-containing feed stream in a gaseous form under pressure to an inlet of the first fluidized catalytic reactor; (5) converting a portion of the oxygenate-containing feed stream into the olefin-containing product stream; and (6) directing the olefin-containing product stream from the first fluidized catalytic reactor to a recovery unit.

TERMS AND CONDITIONS DEFINITIONS

Figure 1:
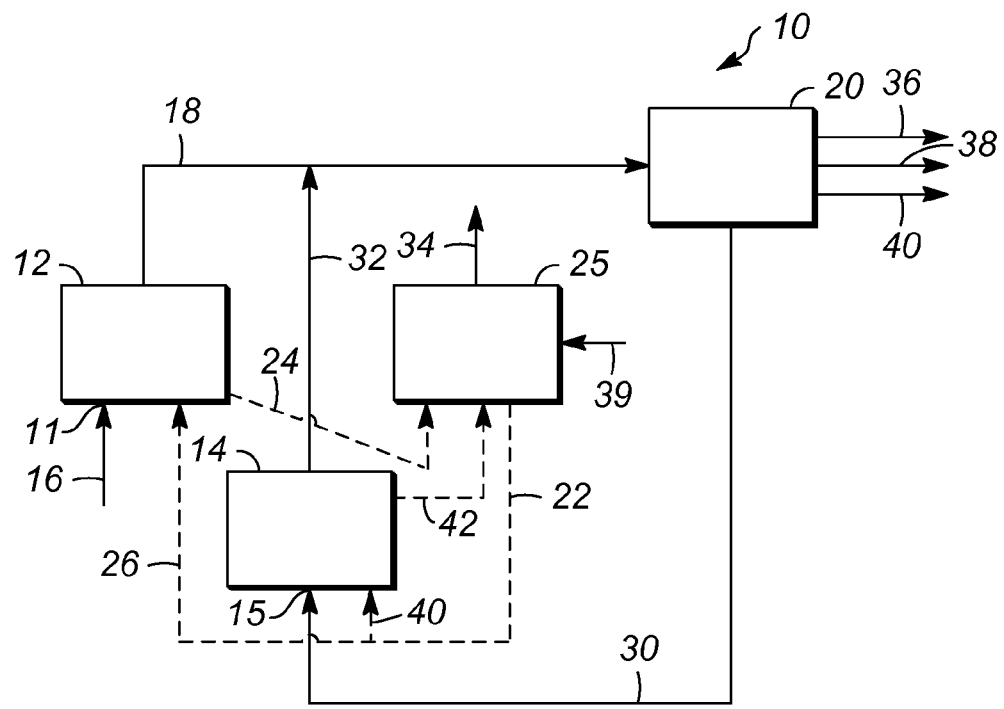
FIG. 1 is a schematic view of a process flow diagram having two fluidized catalytic reactors in parallel relationship.

The following terms and conditions are used in the present specification with the following meanings: (1) A "portion" of a stream means either an aliquot part that has the same composition as the whole stream or a part that is obtained by eliminating a readily separable component therefrom (e.g., if the stream contains hydrocarbons in admixture with steam, then after condensation of a major portion of the steam, it comprises an aqueous portion and a hydrocarbon portion); (2) the presence of necessary compressors and/or pumps is understood when flow is shown from a zone of relatively low pressure to a zone of higher pressure; (3) the presence of necessary heating and/or cooling means is implied when flow is shown between zones operating at different temperatures; (4) the term "light olefins" means ethylene, propylene and mixtures thereof; (5) the term "heavy olefin" means an olefin having a molecular weight greater than propylene; (6) the expression "OTP" process means a process for converting an oxygenate to propylene and in a preferred embodiment when the oxygenate is methanol the OTP process is referred to as an "MTP" process herein; (7) the term "oxygenate" means an oxygen-substituted aliphatic hydrocarbon containing 1 to 10 carbon atoms include aliphatic alcohols, ethers, and carbonyl compounds (e.g., aldehydes, ketones, carboxylic acids, and the like) and mixtures of these materials; (8) the term "dual-function" means that the OTP catalyst catalyzes both the OTP reactions and an olefin interconversion reactions necessary to convert $C_2$ and $C_4^+$ olefins to propylene; (9) the term "highly unsaturated hydrocarbon" means a hydrocarbon which contains two or more double bonds or a triple bond in its structure; and (10) the term "fluidized bed" or "fluidized catalytic" refers to a condition in which particles of a catalyst are entrained or lifted by a pressurized stream of gas or liquid typically against gravity.

DETAILED DESCRIPTION OF THE INVENTION

In a preferred form of the invention, the oxygenates include lower straight or branched chain alcohols, and their unsaturated counterparts. More preferably the oxygenates include methanol, dimethyl ether (DME), ethanol, diethyl ether, methylethylether, formaldehyde, dimethyl ketone, acetic acid, and mixtures thereof. In a most preferred form of the invention, a feedstream contains methanol or dimethylether or mixtures thereof.

In a preferred form of the OTP conversion step, the oxygenate feed is catalytically and selectively converted in a first reaction zone to propylene and by-product hydrocarbons containing aliphatic moieties such as—but not limited to—methane, ethane, ethylene, propane, butylene, butane and limited amounts of other higher carbon number aliphatics by contacting the feedstock with a dual-function OTP catalyst at effective OTP conditions. This OTP conversion step also forms minor amounts of highly unsaturated hydrocarbons, such as dienes and acetylenic hydrocarbons, and aromatic hydrocarbons. A diluent is not absolutely required but is a useful option to maintain the selectivity of the OTP catalyst to produce light olefins, particularly propylene. The use of a diluent such as steam can provide certain equipment cost and thermal efficiency advantages as well as lowering the partial pressure of the oxygenate reactants, thereby increasing selectivity to olefins. The phase change between steam and liquid water can also be employed to advantage in transferring heat between the feedstock and the reactor effluent, and the separation of the diluent from the product requires only a simple condensation step to separate water from the light olefin products.

A diluent is thus preferably used in the reaction zones in order to control partial pressure of the oxygenate reactant to provide a heat sink for the net exothermic reactions occurring therein and to shift the overall reaction selectivity towards propylene. Suitable diluents for use in the reaction zones include helium, argon, nitrogen, carbon monoxide, carbon dioxide, hydrogen, water, $C_1$ through $C_5$ paraffins, aromatic hydrocarbons and mixtures of these materials. Preferred diluents are steam, methane, an aromatic compounds, and mixtures thereof. Preferred diluents are relatively inert at the conditions maintained in the reaction zones. An especially preferred diluent is steam since it is relatively easily recovered from the effluent stream utilizing condensation techniques. The amount of diluent used will be selected from the range of 0.1:1 to 12:1 and more typically from about 0.1:1 to 5:1 moles of diluent per mole of oxygenate in order to lower the partial pressure of the oxygenates to a level which favors production of propylene. All embodiments of the present invention envision recycling to this first reaction zone of at least a portion of an ethylene-rich by-product stream that contains significant amounts of ethylene and minor amounts of C2 saturated hydrocarbons. This C2 olefin recycle stream will thus furnish saturated C2 hydrocarbon diluent to the first reaction zone and therefore the amount of diluent that must be added to the first reaction zone in order to achieve the target diluent to oxygenate mole ratio will diminish once the first reaction zone is started up and C2 by-product recycle initiated.

The present invention utilizes a separate (or second) reaction zone for interconversion of the heavy olefin by-product stream, (i.e., the $C_4^+$ stream) recovered from the effluent from the OTP conversion step.

The conversion conditions used in the first reaction zone are carefully chosen to favor the production of propylene from the oxygenate charged in the feed. In a preferred form of the invention, oxygenate conversion temperatures will be from about 325° C. to about 500° C. The lower portion of this oxygenate conversion temperature range with certain catalysts is known to favor the production of propylene with the upper portion favoring the production of ethylene at the expense of propylene. Preferred inlet temperatures into the reaction zones are therefore in the range of 350° to 450° C., more preferably in the range of about 375° to 425° C. and most preferably in the range of 375° to 400° C. Because water will be present in the OTP reaction zone, this temperature range will promote catalyst stability.

The conversion conditions employed in the separate interconversion reactor is mildly endothermic, the inlet temperature into this interconversion zone is set at a relatively high value with reference to the maximum or peak temperature experienced in the OTP reaction zones (which is typically at or near the outlet of the reactor in this zone) since the balance of the OTP reactions and $C_2$ olefin interconversion reactions are strongly exothermic. In a preferred form of the present invention, the inlet temperature into the second interconversion reaction zone (or into each reactor if multiple reactors are utilized) is at least 15° C. higher than the inlet and/or the maximum temperature reached in the OTP reaction zone. Best results are obtained when this inlet temperature is set so that it is 15° to 25° C., or more, higher than the maximum temperature experienced in the first OTP reaction zone. The second reactor may be operated at a temperature between 450° and 650° C. at the outlet, more preferably in the range of about 500° to 600° C. and most preferably in the range of 525° to 550° C.

A diluent may be used in the interconversion reactor to control the partial pressure of the heavy olefin reactant used therein and to provide an additional heat source for the endothermic interconversion reaction. Suitable diluents can be chosen from those previously set forth in connection with the operation of the OTP reaction zone. Preferred diluents include steam, methane, a mixture of aromatic compounds that are by-products of the OTP reaction, and a mixture of $C_6^+$ olefins, paraffins and aromatics that are by-products of the OTP reactions performed in the OTP reactor and are typically recovered as an olefin-rich gasoline stream in downstream separation facilities as will be explained in conjunction with the discussion of the figures. Of these preferred diluents, steam involves the risk of hydrothermal deactivation of the dual-function catalyst used in the interconversion reactor if steam is used in high concentration but is typically used because of its ability to control and/or prevent coke formation in heaters, heat exchangers and reactor internals, its ready availability, its ease of separability from the products of the interconversion reaction and because it can be used at a much lower concentration than in the OTP reaction zone. The amount of diluent preferably used in the interconversion reaction zone corresponds 0.001:1 to 1:1 moles of diluent per mole of $C_4^+$ olefin charged to this zone and more preferably to a mole ratio of 0.01:1 to 0.5:1. Unlike the situation with respect to the OTP reaction zone it is to be noted that since $H_2O$ is not a by-product of the $C_4^+$ interconversion reactions performed in the interconversion reactor, there is typically no net make of diluent across this zone so that the effective amount of diluent used in the interconversion reactor is the amount charged thereto. However, it is within the scope of the present invention to charge some oxygenate to the interconversion reactor in an amount sufficient to off-set the endothermic interconversion reactions arising therein.

Both the oxygenate to propylene conversion and the $C_4^+$ olefin interconversion steps are effectively carried out over a wide range of pressures including inlet total pressures between about 0.1 atm (10.1 kPa) up to about 100 atm (10.1 MPa) but it is well known that the formation of lighter olefins like propylene are favored at low pressure conditions. It is thus preferred for both of these steps to use an inlet pressure in the range of about 1 to 3 atm (101.3 to 304 kPa) and best results are achieved at about 136 to 343 kPa (5 to 35 psig).

The contact time of the reactants with the dual-function catalyst is ordinarily measured in relative terms of a weight hourly space velocity (WHSV) which is calculated for the OTP conversion step on the basis of mass hourly flow rate of the sum of the mass of oxygenate reactants passed to the first reaction zone plus the mass of any reactive hydrocarbon material present in the feedstream or any of the recycle streams passed to the first reaction zone divided by the mass of the dual-function catalyst present in the first reaction zone. The WHSV for the $C_4^+$ olefin interconversion step is likewise calculated on the basis of mass hourly flow rate of the sum of the mass of $C_4^+$ olefin by-product stream passed thereto plus the mass of any reactive hydrocarbons present in any recycle stream or diluent stream passed thereto divided by the mass of the second dual-function catalyst present in the second reaction zone. Those skilled in the art will recognize that the contact time of the reactants with the catalyst is proportional to the inverse of the WHSV such that as the WHSV increases contact time decreases and conversely a decrease in WHSV produces an increase in contact time. WHSV for use in both the OTP reactor and the interconversion reactor associated with the present invention can range from about 0.1 to 100 hr$^{-1}$, with a preferred range being about 0.5 to 20 hr$^{-1}$, with best results ordinarily attained in the range of 0.5 to 10 hr$^{-1}$.

In one preferred form of the invention, both the oxygenate-to-propylene conversion and the $C_4^+$ olefin interconversion steps utilize the same dual-function catalyst system. Preferably, the dual-function catalyst system has the capability of converting oxygenates to propylene as well as the capability of interconverting olefins other than propylene to propylene. Any of the catalytic materials known to the art that have the capability to catalyze these two reactions are suitable ingredients for use in the catalysts used in the present invention. The preferred dual-function catalyst system contains a molecular sieve as the active ingredient and more specifically the molecular sieve has relatively small pores characterized as not larger than those associated with the 10 member pores of ZSM-5 and ZSM-11. Certain of the molecular sieves useful in the present invention have pores with an average effective diameter of less than 5 Å.

Suitable zeolitic molecular sieves in the calcined form may be represented by the general formula:

$$Me_{2/n}O:Al_2O_3:xSiO_2:yH_2O$$

where Me is a cation, x is the framework $SiO_2$ to $Al_2O_3$ ratio and has a value from about 2 to infinity, n is the cation valence and y has a value of about 2 to 100 or more and more typically about 2 to 25.

Zeolites which may be used include chabazite—also referred to as Zeolite D, clinoptilolite, erionite, ferrierite, mordenite, Zeolite A, Zeolite P, ZSM-5, ZSM-11, and MCM-22. Zeolites having a high silica content (i.e., those having framework silica to alumina ratios greater than 100 and typically greater than 150 with good results achieved at a silica to alumina mole ratio of about 150:1 to 800:1) are especially preferred. One such high-silica-content zeolite having the structure of ZSM-5 is silicalite, as the term used herein includes both the silicapolymorph disclosed in U.S. Pat. No. 4,061,724 and also the F-silicate disclosed in U.S. Pat. No. 4,073,865. Best results are obtained with ZSM-11 or ZSM-5 or a mixture thereof.

The most preferred zeolitic dual-function catalyst for use in both conversion steps of the present invention is a zeolite having the structural configuration of ZSM-5 or ZSM-11, sometimes in the literature referred to as having a "pentasil-type" structure.

Non-zeolitic molecular sieves useful in the dual-function catalysts used in the present invention include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of aluminum and is at least 0.01, z is the mole fraction of phosphorous and is at least 0.01 and x+y+z=1. When EL is a mixture of metals, x represents the total amount of the element mixture present. Preferred elements (EL) are silicon, magnesium and cobalt with silicon being especially preferred. In a preferred form of the invention the non-zeolitic molecular sieve catalyst are SAPO catalyst and even more preferably SAPO-34 or SAPO-11.

In one preferred form of the invention where the dual-function catalyst is a blend of a zeolite-type molecular sieve catalyst and a non-zeolite-type molecular sieve catalyst, the blend will contain a portion of SAPO-34 and preferably in a principal amount greater than 50% by weight. In another preferred form of the invention, the catalyst system will include a zeolitic material of a highly siliceous ZSM-5 or ZSM-11 type of material that will serve to catalyze reactions in both OTP and interconversion reaction zones operating under different conditions set to favor the respective reaction. Hence, under the different conditions in each respective reaction zone, the zeolitic catalyst promotes the desired reaction.

In an even more preferred form of the invention, the dual-function catalyst system is a mixture of a zeolitic catalyst with a non-zeolitic catalyst. This mixed catalyst embodiment can be accomplished either using a physical mixture of particles containing the zeolitic material with particles containing the non-zeolitic material or the catalyst can be formulated by mixing the two types of material into a suitable binding matrix in order to form particles having both ingredients present therein.

The present invention uses two separate reaction zones containing particles of the dual-function catalyst described hereinbefore. In the case where the dual-function catalysts used in these two zones are a blend of different catalyst compositions or a mixture of different catalysts on the same particle then the catalyst that is most active in the first reaction zone that performs the OTP conversion and $C_2$ olefin interconversion step is referred to as the first dual-function catalyst and the catalyst that is most active in the second reaction zone that performs the $C_4^+$ olefin interconversion step is called the second dual-function catalyst. In the preferred case exemplified in the figures, the same dual-function catalyst is used to catalyze both the OTP conversion and $C_2$ olefin interconversion step and the $C_4^+$ interconversion step in separate reaction zones.

The present invention further includes an optional selective hydrogenation treatment step to selectively hydrogenate highly unsaturated hydrocarbons such as dienes and/or acetylenic hydrocarbons that are formed in the OTP conversion step in minor amounts (i.e., less than 2 wt-% of the amount of oxygenate feed converted and typically about 0.01 to 1 wt-% of the amount converted). While these highly unsaturated hydrocarbons do not represent a substantial source of propylene yield loss, it has been found that they are a very significant contributor to the rate of coke deposition on the preferred dual-function catalyst. The selective hydrogenation conditions utilized in this treatment step are selected from conditions known to those of skill in the art to be effective to convert highly unsaturated hydrocarbons to the corresponding olefins while minimizing or eliminating any over-hydrogenation to the corresponding fully saturated hydrocarbon.

One preferred form of the present invention utilizes moving bed technology in the OTP conversion and $C_2$ olefin interconversion step and in the separate $C_4^+$ olefin interconversion step in order to enhance the selectivity of the overall process for propylene production. The use of moving bed technology in a classical MTO process is known and is shown in U.S. Pat. No. 5,157,181.

The reactors of the present invention utilize flowing catalyst. In a moving bed catalytic reactor, catalyst is allowed to gradually flow downwardly by gravity to exit the bottom of the reactor for transport to the top of a regenerator. Catalyst may be allowed to flow gradually downwardly to the bottom of the regenerator for transport to the top of the reactor. An additive such as yttrium oxide can be used to prolong catalyst activity during long reaction cycles in both the OTP conversion and the olefin interconversion reactors. In a preferred form of the present invention, fluidized bed technology is utilized in both reaction zones to enhance the selectivity of the overall process for propylene production. Fluidized bed reactors and regeneration systems suitable for use in accordance with the present invention are well known in the art and have been widely employed commercially for use in other reaction processes. In a fluidized bed catalytic reactor catalyst typically flows against gravity propelled by a fluidizing gas which may be a gaseous reactant.

Fluidized bed catalytic reaction zones for use in the instant invention can be configured in a number of ways, for example, the dual-function catalyst particles can be introduced to a lower section of the first or second reaction zone in a pressurized stream of gaseous reactants or light diluent. The dual-function catalyst is contacted with the feedstream or by-product stream either in a countercurrent direction to the catalyst movement or in a concurrent direction. In a preferred aspect of the present invention the feedstream or by-product stream flow is concurrent to the catalyst flow, that is, the oxygenate feedstream or the $C_4^+$ olefin by-product feedstream is introduced into a lower portion of the reaction zone and withdrawn from an upper portion thereof. In this case, gaseous reactants serve as the fluidizing gas to lift the catalyst in the reaction zone from a lower bed, inlet or distributor of the reactor to an upper product outlet. A gas-solid separation device such as a cyclone may intercept the product gas-catalyst mixture and separate the catalyst from the gases which will exit through a product outlet.

During the traversal through the reactors, a carbonaceous material, i.e., coke, is deposited on the catalyst as it flows through the reactors. The carbonaceous deposit material has the effect of reducing the number of active sites on the catalyst which thereby affects the extent of the overall conversion and the selectivity to propylene. A portion of the coked dual-function catalyst is thus withdrawn from the reactors after separation from the product gas and regenerated to remove at least a portion of the coke therefrom. Two separate regeneration zones can be used to avoid mixing the catalyst particles from different zones together. U.S. Pat. No. 4,498,973 discloses regeneration of two separate and distinct catalysts in a single regeneration zone without commingling the catalyst particles. In the preferred case, the coked particles from both zones can be mixed together and charged or separately charged to a common regeneration zone. It is within the scope of the present invention in this last case to charge at least a portion of the partially coked catalyst particles withdrawn from the second reaction zone to the OTP reaction zones. This can be advantageous when the selectivity of the dual-function catalyst to propylene in the first reaction zone is improved due to the partial coverage of active sites with fresh coke deposits.

The carbonaceous material is removed from the catalyst by oxidative regeneration wherein a moving bed of the catalyst particles withdrawn from the reactors is contacted with an oxygen-containing gas stream at sufficient temperature and oxygen concentration to allow the desired amount of the carbonaceous materials to be removed by combustion from the catalyst.

DETAILED DESCRIPTION OF THE DRAWING

The convention used in these figures is that the flow of feed materials, intermediate materials and product materials is represented by solid lines and the flow of catalyst to and from the reaction zones is shown by dotted lines. The dual-function catalyst is shown as being transported by a transport medium which is preferably steam, nitrogen or any of the other inert diluents previously described. The preferred catalyst transport medium is steam due to its substantial presence in the first and second reaction zones. The details associated with the mechanical equipment necessary to engage, transport and disengage the dual-function catalyst particles as they flow from reaction zone to reaction zone and to the regeneration zone 25 such as cyclonic separation, are well known to those skilled in the art.

The following description of a highly preferred embodiment of the process of the present invention is made with reference to the attached figures. In the interest of simplifying the description of the invention in order to facilitate understanding, the figures do not contain representations of cyclones, heaters, heat exchangers, coolers, valves, control means and other conventional items that are well known to those of ordinary skill in the chemical engineering art except where their presence is essential to the understanding of the present invention. In this highly preferred embodiment the first and second dual-function catalysts are mixed or incorporated on the same particle, so only one regeneration zone, moving or fluidized bed regenerator 25, is therefore necessary unless there are other reasons for keeping the catalyst from respective reaction zones separate.

FIG. 1 shows one preferred reactor system 10 having a first fluidized catalytic bed reactor 12 and a second fluidized catalytic bed reactor 14 arranged in parallel flow configuration. The first fluidized catalytic reactor 12 may embody a bubbling or turbulent bed or a fast fluidized or transport catalytic flow regime. The second reactor 14' may embody a bubbling or turbulent bed or a fast fluidized or transport catalytic flow regime. The first fluidized bed reactor 12 is operated under conditions to perform the OTP conversion reaction of an oxygenate-containing feed stream 16 introduced by inlet 11 to an olefin-containing product stream 18. In a preferred form of the invention, the preferred olefin in the olefin-containing product stream is propylene. The olefin-containing product stream 18 is in fluid communication with a light-olefin recovery process (LORP) system 20. A regenerated dual-function catalyst is supplied from regenerator 25 to the first fluidized bed reactor 12 through lines 22 and 26 and removed through line 24 and conveyed therein to a regenerator 25. An oxygen-containing gas is added to the regenerator by line 39 to combust coke from the catalyst. Flue gas is exhausted from regenerator 25 in line 34.

The LORP system 20 separates propylene from non-propylene components such as ethylene, water and $C_4^+$ olefins, paraffins and aromatics. The LORP system 20 may comprise one or more separation units which produce an ethylene stream 36, a portion or all of which may be recycled (not shown) to the first reactor 12, a propylene product stream in line 38 which is recovered, a water stream 40, which may be recycled (not shown) in whole or in part to the first reactor 12, and a C4+ heavies stream 30, which is conveyed under pressure through line 30 to an inlet 15 of the second fluidized bed reactor 14. Some of the heavies stream can also be transported (not shown) to the first reactor 12 to serve as a heat sink. As a portion of the product stream in line 18 is circulated to the second reactor 14 from the LORP system 20, the second reactor is in down stream partial fluid communication with the first reactor 12.

The second fluidized bed reactor 14 is operated under conditions to convert the heavy olefins from the LORP in line 30 to a propylene-containing effluent or product stream 32. The product stream 32 is conveyed to the LORP system 20, and, in a preferred form of the invention, the product stream 32 will intersect and mix with the product stream 18 such that line 18 is in down stream fluid communication with line 32.

The regenerator 25 supplies regenerated catalyst to the second fluidized bed reactor 14 through lines 22 and 40 and coked catalyst is transported through line 42 to the regenerator 25. Accordingly, the catalyst regenerator 25 is in downstream fluid communication with the first reactor 12 and the second reactor 14 by lines 24 and 42, respectively. Additionally, first reactor 12 and second reactor 14 are in downstream fluid communication with regenerator 25 via lines 22, 26 and 40, respectively.

Figure 2:
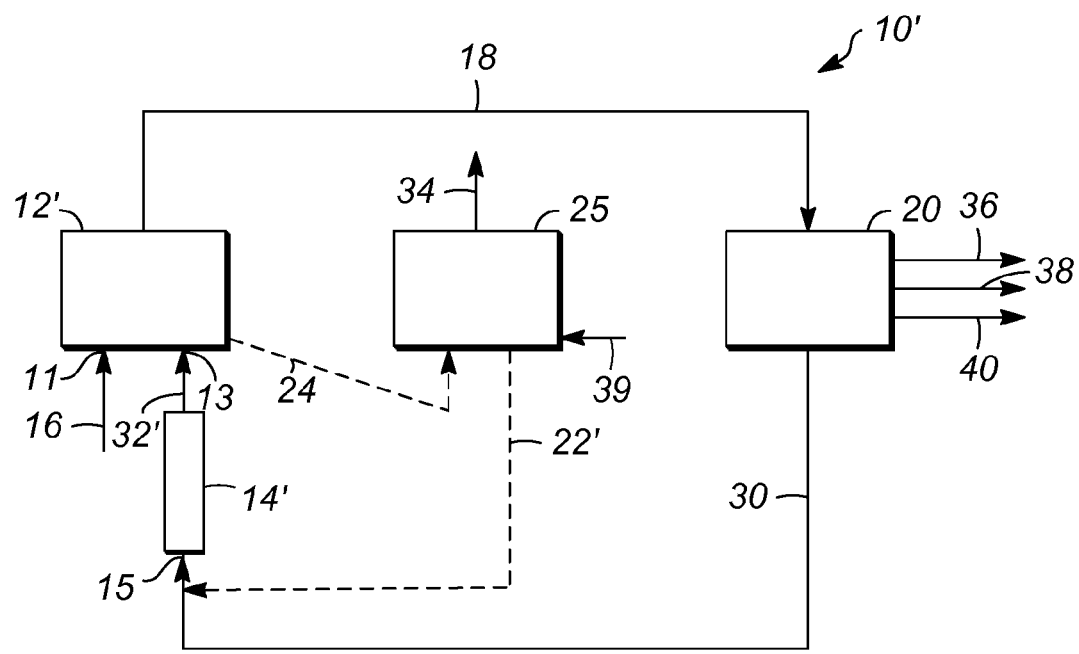
FIG. 2 is a schematic view of a process flow diagram having two fluidized catalytic reactors in series relationship.

FIG. 2 shows another preferred reactor system 10' having a first and a second fluidized bed reactors 12', 14' arranged in serial flow configuration. The first reactor 12' may embody a bubbling, turbulent or a fast fluidized or transport flow regime. The second reactor 14' may embody a fast fluidized or transport catalytic flow regime. Corresponding elements with different configurations are designated with a prime symbol (') in FIG. 2. Like numbers have been used to refer to like elements. The principal differences between the reactor system shown in FIG. 1 and FIG. 2 is that FIG. 2 shows the effluent stream 32' from the second fluidized bed reactor 14' is transported to an inlet 13 of the first fluidized reactor 12'. Also, regenerated catalyst is transported through line 22' only to the second fluidized bed reactor 14', instead of also to the first fluidized bed reactor as in the flow scheme of FIG. 1. However, an alternative embodiment of FIG. 2 may have a separate transport (not shown) of regenerated catalyst from regenerator 25 to the first reactor 12' in addition to the transport of regenerated catalyst to the second reactor 14' in line 22'. Catalyst and product gases from the second reactor 14' flow together through line 32' without undergoing separation before entering inlet 13 of the first reactor 12'. Hence, the second reactor 14' is directly communicating with the first reactor 12'. Regenerated catalyst from line 22' flows through the second reactor 14 before entering the first fluidized bed reactor 12. In the foregoing embodiment, the first reactor 12' is in complete downstream fluid communication with the second reactor 14' and the second reactor 14' is in partial down steam fluid communication with the first reactor 12' through lines 18 and 30. All, some or no coked catalyst may be transported from the second fluidized bed reactor 14' through line 32' to the first fluidized reactor 12'. It is contemplated also in an embodiment that at least some separation between product gas and catalyst in the second reactor may occur before sending the product gas and some or no catalyst from the second reactor 14' to the first reactor 12'. In an embodiment, the regenerated catalyst is added to the feed to the second reactor 14' in line 22' before entering the second reactor 14'. The feed and catalyst, however, may be charged separately to the second reactor 14'.

Hot regenerated catalyst from the regenerator 25 ensures the endothermic cracking reaction in the second reactor 14' proceeds. Moreover, a feed heater (not shown) may also be utilized to heat the feed in line 30 to the second reactor 14'. The vaporous product and catalyst exiting the second reactor 14' and entering the first reactor 12' is cooler which favors moderating the temperature of the exothermic OTP reaction in the first reactor 12'. Catalyst coolers (not shown) may be utilized to assist heat management in the first reactor 12'.

Hot regenerated catalyst from the regenerator 25 ensures the endothermic cracking reaction in the second reactor 14' proceeds. Moreover, a feed heater (not shown) may also be utilized to heat the feed in line 30 to the second reactor 14'. The vaporous product and catalyst exiting the second reactor 14' and entering the first reactor 12' is cooler which favors moderating the temperature of the exothermic OTP reaction in the first reactor 12'. Catalyst coolers (not shown) may be utilized to assist heat management in the first reactor 12'.

In a preferred form of the invention, the dual-function catalyst utilized in the first and second fluidized bed reactors 12, 14 is a blend of a zeolite-type molecular sieve catalyst and a non-zeolite-type molecular sieve catalyst. In a preferred form of the invention, the zeolite-type molecular sieve catalyst is either a ZSM-5 or ZSM-11 type catalyst. In a preferred form of the invention the non-zeolite-type molecular sieve catalyst will be a SAPO type catalyst and more preferably SAPO-34. In another preferred form of the invention with both catalysts impregnated on the same particle, both zeolite-type and non-zeolite-type molecular sieves would be mixed in a slurry of binder and support as is known and spray dried to make the dual-catalyst particle composition. The weight ratio of zeolite-type molecular sieve to non-zeolite-type molecular sieve should be from 1.0-0.9 to 0.9-0.1, more preferably from 0.25-0.75 to 0.75-0.25 and most preferably from 0.4-0.6 to 0.6-0.4.

The invention claimed is:

1. A method for converting an oxygenate-containing feed stream to an olefin-containing product stream comprising:
providing a first fluidized catalytic reactor for converting methanol to propylene and heavy olefins;
providing a second fluidized catalytic reactor connected to the first fluidized bed reactor for cracking heavy olefins having four carbon atoms or greater into propylene;
providing a catalyst system in a fluidized stream into the first fluidized catalytic reactor and into the second fluidized catalytic reactor, wherein the catalyst system comprises a first catalyst and a second catalyst, the first catalyst being a non-zeolite molecular sieve catalyst and the second catalyst being a zeolite molecular sieve catalyst, and wherein the inlet temperature of the second reactor is at least 15° C. higher than the inlet of the first reactor;
providing the oxygenate-containing feed stream in a gaseous form under pressure to an inlet of the first fluidized bed reactor;
fluidizing the catalyst system with the gaseous oxygenate-containing feed stream from said inlet against gravity;
converting a portion of the oxygenate-containing feed stream into the olefin-containing product stream;
directing the olefin-containing product stream from the first fluidized catalytic reactor to a recovery unit; and
passing catalyst from the first fluidized catalytic reactor and the second catalytic reactor to a catalyst regenerating unit for removing a portion of a coke deposit from the catalyst particles.

2. The method of claim 1 further comprising directing a portion of the olefin-containing product stream comprising heavy olefins having four carbon atoms or greater from the recovery unit in a gaseous form under pressure to an inlet of to the second catalytic reactor and fluidizing the catalyst system with the gaseous olefin-containing product stream comprising heavy olefins from said inlet against gravity.

3. The method of claim 2 further comprising cracking a portion of the heavy olefins in the olefin-containing product stream into a propylene-containing product stream in the second fluidized catalytic reactor.

4. The method of claim 3 further comprising directing the propylene-containing product stream into the olefin-containing product stream.

5. The method of claim 3 further comprising directing the propylene-containing product stream into an inlet of the first fluidized catalytic reactor.

* * * * *